US012599554B2

(12) United States Patent
Dordunoo

(10) Patent No.: US 12,599,554 B2
(45) Date of Patent: Apr. 14, 2026

(54) PHARMACEUTICAL FORMULATIONS COMPRISING TADALAFIL

(71) Applicant: KYDES PHARMACEUTICALS, LLC, Rosedale, MD (US)

(72) Inventor: Stephen Kwaku Dordunoo, Rosedale, MD (US)

(73) Assignee: KYDES PHARMACEUTICALS LLC, MD (US)

( * ) Notice: Subject to any disclaimer, the term of this patent is extended or adjusted under 35 U.S.C. 154(b) by 567 days.

(21) Appl. No.: 18/007,282

(22) PCT Filed: Jul. 28, 2021

(86) PCT No.: PCT/US2021/043524
§ 371 (c)(1),
(2) Date: Jan. 27, 2023

(87) PCT Pub. No.: WO2022/026591
PCT Pub. Date: Feb. 3, 2022

(65) Prior Publication Data
US 2023/0285283 A1 Sep. 14, 2023

Related U.S. Application Data

(60) Provisional application No. 63/058,185, filed on Jul. 29, 2020.

(51) Int. Cl.

| | |
|---|---|
| ***A61K 9/00*** | (2006.01) |
| ***A61K 9/08*** | (2006.01) |
| ***A61K 9/20*** | (2006.01) |
| ***A61K 9/48*** | (2006.01) |
| ***A61K 31/135*** | (2006.01) |
| ***A61K 31/137*** | (2006.01) |
| ***A61K 31/40*** | (2006.01) |
| ***A61K 31/435*** | (2006.01) |
| ***A61K 31/437*** | (2006.01) |
| ***A61K 31/4525*** | (2006.01) |

(Continued)

(52) U.S. Cl.
CPC ............ *A61K 9/006* (2013.01); *A61K 9/0034* (2013.01); *A61K 9/08* (2013.01); *A61K 9/2013* (2013.01); *A61K 9/2018* (2013.01); *A61K 9/2027* (2013.01); *A61K 9/2031* (2013.01); *A61K 9/2054* (2013.01); *A61K 9/485* (2013.01); *A61K 9/4858* (2013.01); *A61K 9/4866* (2013.01); *A61K 9/4875* (2013.01); *A61K 31/135* (2013.01); *A61K 31/137* (2013.01); *A61K 31/40* (2013.01); *A61K 31/435* (2013.01); *A61K 31/437* (2013.01); *A61K 31/4525* (2013.01); *A61K 31/48* (2013.01); *A61K 31/485* (2013.01); *A61K 31/4985* (2013.01); *A61K 31/517* (2013.01); *A61K 31/568* (2013.01); *A61K 38/095* (2019.01); *A61K 45/06* (2013.01); *A61K 47/10* (2013.01); *A61K 47/12* (2013.01); *A61K 47/14* (2013.01); *A61K 47/18* (2013.01); *A61K 47/22* (2013.01); *A61K 47/26* (2013.01); *A61K 47/34* (2013.01); *A61P 15/00* (2018.01); *A61P 15/10* (2018.01)

(58) Field of Classification Search
CPC .......... A61K 9/006; A61K 9/08; A61K 31/40; A61K 31/4525; A61K 31/485; A61K 31/4985; A61K 31/568; A61K 47/12; A61K 47/22; A61K 9/0034; A61K 9/2013; A61K 9/2018; A61K 9/2027; A61K 9/2031; A61K 9/2054; A61K 9/485; A61K 9/4858; A61K 9/4866; A61K 9/4875; A61K 31/135; A61K 31/48; A61K 38/095; A61K 45/06; A61K 47/10; A61K 47/14; A61K 47/26; A61K 47/34; A61P 15/10
See application file for complete search history.

(56) References Cited

U.S. PATENT DOCUMENTS 10,111,833 B2 10/2018 Potta et al.
2007/0032529 A1* 2/2007 Takagi .............. A61K 31/4184 548/368.4

(Continued)

FOREIGN PATENT DOCUMENTS

BR 102015015988 A8 2/2018
CN 109796461 A * 5/2019

(Continued)

OTHER PUBLICATIONS

English translation for CN 109796461 A (Year: 2019).*

(Continued)

*Primary Examiner* — Sin J Lee
(74) *Attorney, Agent, or Firm* — Jordan IP Law, LLC

(57) ABSTRACT

Provided are stable, concentrated, and palatable solutions suitable for sublingual and/or transurethral administration containing tadalafil, with or without other active ingredients to address comorbidities, in a liquid vehicle or solvent selected from propylene carbonate, 2-pyrrolidone, dimethyl isosorbide, dimethyl acetamide, n-methyl-2-pyrrolidone, ethanol, water, oleic acid, and isopropyl myristate. The solutions have low irritancy for sublingual tissues and a-are compatible with commercial atomizers. The invention is further directed to methods of treating male erectile dysfunction and/or comorbidities by administering an effective amount of the pharmaceutical formulations comprising tadalafil, with or without other active ingredients, to a patient in need of such treatments.

16 Claims, 2 Drawing Sheets

(51) Int. Cl.

| | |
|---|---|
| ***A61K 31/48*** | (2006.01) |
| ***A61K 31/485*** | (2006.01) |
| ***A61K 31/4985*** | (2006.01) |
| ***A61K 31/517*** | (2006.01) |
| ***A61K 31/568*** | (2006.01) |
| ***A61K 38/095*** | (2019.01) |
| ***A61K 45/06*** | (2006.01) |
| ***A61K 47/10*** | (2017.01) |
| ***A61K 47/12*** | (2006.01) |
| ***A61K 47/14*** | (2017.01) |
| ***A61K 47/18*** | (2017.01) |
| ***A61K 47/22*** | (2006.01) |
| ***A61K 47/26*** | (2006.01) |
| ***A61K 47/34*** | (2017.01) |
| ***A61P 15/00*** | (2006.01) |
| ***A61P 15/10*** | (2006.01) |

(56) References Cited

U.S. PATENT DOCUMENTS

| | | | | |
|---|---|---|---|---|
| 2007/0088012 | A1* | 4/2007 | Seo | A61P 5/00 424/448 |
| 2007/0122355 | A1 | 5/2007 | Monteith et al. | |
| 2009/0221570 | A1 | 9/2009 | Haning et al. | |
| 2015/0005307 | A1 | 1/2015 | Sams et al. | |
| 2015/0366805 | A1* | 12/2015 | Monsuur | B01J 20/103 424/489 |
| 2016/0375018 | A1* | 12/2016 | Lee | A61K 31/506 514/250 |
| 2020/0214990 | A1 | 7/2020 | Fan et al. | |
| 2021/0369619 | A1* | 12/2021 | Nandi | A61K 31/706 |
| 2023/0372238 | A1* | 11/2023 | Mehta | A61K 31/519 |

FOREIGN PATENT DOCUMENTS

| | | | |
|---|---|---|---|
| CN | 111110633 | A | 5/2020 |
| EP | 2216329 | A1 | 8/2010 |
| KR | 101484481 | B1 | 1/2015 |
| WO | 2008100933 | A2 | 8/2008 |
| WO | 2008144061 | A2 | 11/2008 |
| WO | 2017069533 | A1 | 4/2017 |
| WO | 2017201071 | A1 | 11/2017 |
| WO | 2019130052 | A1 | 7/2019 |

OTHER PUBLICATIONS

Vrentzos et al ("Dyslipidemia as a Risk Factor for Erectile Dysfunction", Current Medicinal Chemistry, vol. 14 (2007), p. 1765-1770) (Year: 2007).*

Hamishehkar, H. et al., "The relationship between solubility and transdermal absorption of tadalafil", Advanced Pharmaceutical Bulletin, 2015, vol. 5, No. 3, pp. 411-417.

International Search Report for PCT/US2021/043524, mailed Nov. 22, 2021.

Office Action for Canada Application No. 3,187,455, mailed Jan. 16, 2025, four pages.

Extended European Search Report, Application No. 21850325.8, Dated Jul. 17, 2024, 14 pages.

* cited by examiner

PHARMACEUTICAL FORMULATIONS COMPRISING TADALAFIL

CROSS REFERENCE TO RELATED APPLICATIONS

The present application is a U.S. National Phase Patent Application, which claims the benefit of priority to International Patent Application No. PCT/US2021/043524 filed on Jul. 28, 2021, which claims benefit of priority from U.S. Provisional Application No. 63/058,185 filed on Jul. 29, 2020.

TECHNICAL FIELD

The present disclosure is directed to stable, concentrated, and palatable pharmaceutical formulations suitable for buccal and/or sublingual administration containing a phosphodiesterase type 5 (PDE5) inhibitor, with or without other therapeutically active ingredients to address comorbidities associated with erectile dysfunction (ED), and a solvent. The disclosure is further directed to methods of treating male erectile dysfunction and/or comorbidities associated with erectile dysfunction by administering an effective amount of said formulations to a patient in need of such treatment.

BACKGROUND

Erectile dysfunction (ED) is the inability to attain and maintain an erection as a part of normal male sexual function. ED is a common sexual arousal disorder that primarily affects men over the age of 40, with more than 50% of men aged 40 to 69 experiencing some degree of ED. As the global population ages, it is expected that the number of men with ED will increase in the future. For example, it has been estimated that the worldwide prevalence of the condition will be approximately 322 million in 2025 with significant under-reporting due to embarrassment on the part of men.

Erectile dysfunction is often found in association with other disorders, such as premature ejaculation, diabetes, cardiovascular disease, hypertension, dyslipidemia, obesity, depression, benign prostatic hyperplasia, hyperprolactinemia, chronic obstructive pulmonary disease (COPD), lower urinary tract symptoms (LUTS), and testosterone deficiency. Although the etiology of ED is often multifactorial (caused by organic factors, psychogenic factors, or a combination of both), there is evidence that some comorbid conditions, such as diabetes, cardiovascular disease, and hypertension, can be a primary cause of ED. Evidence indicates that over 80% of ED patients have organic causes, of which vascular disease is the most common. The increased occurrence of cardiovascular disease, hypertension, hyperlipidemia, diabetes and, controversially, depression in men with ED may suggest that these conditions share common risk factors. The presence of ED could thus be used as a marker for some of these comorbid conditions.

Since the early 2000s, oral phosphodiesterase type 5 (PDE5) inhibitors including phosphodiesterase type 5 (PDE5) inhibitors such as sildenafil citrate (Viagra®), tadalafil (Cialis®), and vardenafil (Levitra®), have had significant success as a safe and effective oral therapy for the treatment of ED.

PDE5 inhibitors may also be used for the treatment of premature ejaculation. In addition to erectile dysfunction, pre-mature ejaculation also presents a significant health burden. Premature ejaculation (PE) is commonly defined by a short ejaculatory latency, a perceived lack of ejaculatory control; both related to self-efficacy; and distress and interpersonal difficulty. PE can be either lifelong (primary—present since first sexual experiences) or acquired (secondary—beginning later). The International Society of Sexual Medicine's Ad Hoc Committee for the Definition of Premature Ejaculation defines PE as a male sexual dysfunction characterized by ejaculation within about one minute of vaginal penetration (lifelong PE) or a clinically significant and bothersome reduction in latency time to ≤×3 minutes (secondary PE), the inability to delay ejaculation, and negative personal consequences.

Other drugs used in the management of erectile dysfunction include dopamine agonists. The dopamine agonist cabergoline is a synthetic drug, with a long half-life and a high affinity for D2 receptors, that is indicated for treatment of Parkinson's disease and hyperprolactinemic disorders. Dopamine agonists such as apomorphine, ropinirole and cabergoline were observed to increase penile erection and libido in patients with Parkinson's disease. Krueger et al demonstrated that cabergoline induced an acute modification of prolactin plasma levels in healthy men that may be a possible factor modulating their sexual drive and function. De Rosa et al reported normalization of serum prolactin and preserving gonadal function in hyperprolactinemic men after 6 months of cabergoline treatment.

ED is often accompanied by depression, anxiety, poor self-esteem, and compromised interpersonal relationships. ED may also be accompanied by testosterone deficiency in some cases. Due to such factors and embarrassment, the oral formulations of ED therapeutic agents such as phosphodiesterase type 5 (PDE5) inhibitors sildenafil citrate (Viagra®), tadalafil (Cialis®), and vardenafil (Levitra®), are sometimes considered to be inconvenient. Additionally, there are numerous drawbacks with oral therapy such as a long onset of action requiring administration several hours prior to intercourse, high first pass metabolism and low bioavailability, in addition to a requirement to be taken with water, and factors relating to convenience and a need for discreet administration due to embarrassment of men. Various formulations for ED therapeutic agents, such as PDE5 inhibitors, have been investigated such as orodispersible formulations, orally disintegrating formulations, and transdermal formulations. There remains a need for safe, effective, therapeutic formulations that can be administered discreetly, and conveniently.

SUMMARY

The present disclosure is directed to safe, effective, therapeutic formulations for treatment of ED and/or comorbidities associated with ED that can be administered discreetly, and conveniently.

One or more exemplary embodiments of the present disclosure include compositions comprising: (a) an active agent selected from (1) tadalafil or a derivative or analog of tadalafil, or a pharmaceutically acceptable salt thereof, or (2) a combination of tadalafil or a derivative or analog of tadalafil, or a pharmaceutically acceptable salt thereof with a therapeutic agent for the treatment of comorbid diseases or conditions associated with erectile disfunction such as premature ejaculation, diabetes, cardiovascular disorders, hypertension, hyperlipidemia, obesity, depression, benign prostatic hyperplasia, hyperprolactinemic disorders, chronic obstructive pulmonary disease (COPD), lower urinary tract symptoms (LUTS), and testosterone deficiency; and (b) at least one solvent selected from the group consisting of propylene carbonate, 2-pyrrolidone, dimethyl isosorbide, dimethyl acetamide, n-methyl 2-pyrrolidone (NMP), glacial acetic acid, ethanol, water, oleic acid, and isopropyl myristate.

The compositions of the present disclosure are concentrated solutions to be administered in a volume less than 0.2 mL. In one or more exemplary embodiments, the compositions of the present disclosure are sublingual or buccal formulations, such as an oral mist or spray or transurethral dosage formulations.

In one or more exemplary embodiments, the present disclosure relates to a method for the treatment of erectile dysfunction comprising administering an effective amount of the compositions of the disclosure to a patient in need of such treatment.

In one or more exemplary embodiments, the present disclosure relates to a method for the treatment of erectile dysfunction and a comorbid disease or condition associated with erectile dysfunction selected from the group consisting of premature ejaculation, diabetes, cardiovascular disorders, hypertension, hyperlipidemia, obesity, depression, benign prostatic hyperplasia, hyperprolactinemic disorders, chronic obstructive pulmonary disease (COPD), lower urinary tract symptoms (LUTS), and testosterone deficiency.

The features, functions and advantages that have been discussed can be achieved independently in various embodiments or may be combined in yet other embodiment further details of which ca be seen with reference to the following description and drawings.

DRAWINGS

The various advantages of the embodiments will become apparent to one skilled in the art by reading the following specification and appended claims, and by referencing the following drawings in which:

DESCRIPTION

Figure 1:
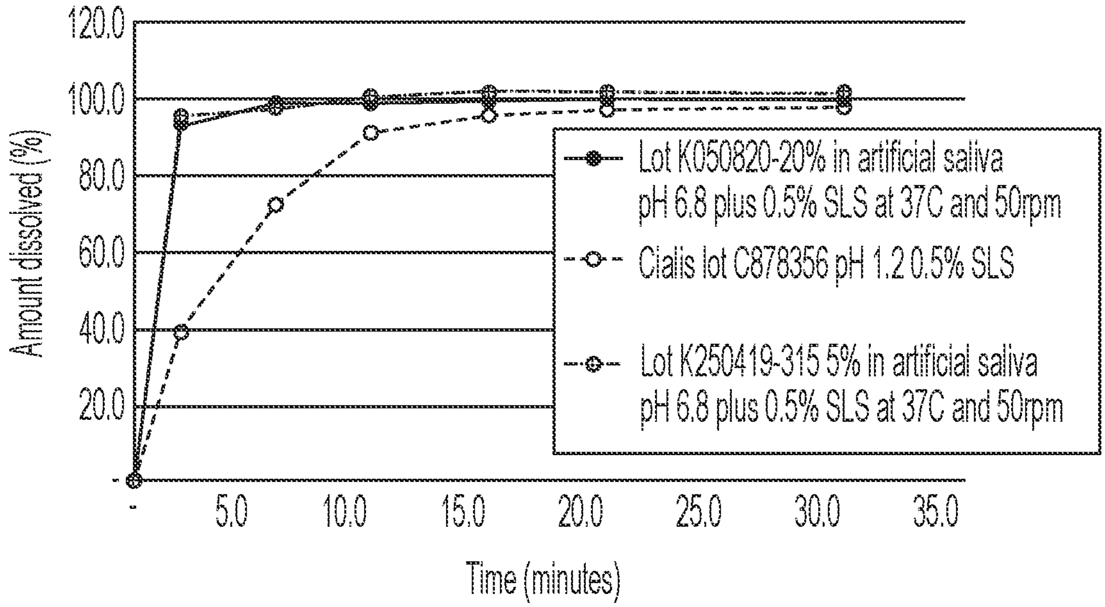
FIG. 1 illustrates the dissolution of tadalafil in artificial saliva (sublingual solution) or 0.1 N HCl (Cialis®) plus 0.5% sodium lauryl-sulfate at 37° C. and 50 rpm.

The present inventor has developed stable, concentrated and palatable pharmaceutical formulations suitable for sublingual, buccal, or transurethral administration containing tadalafil or a derivative or analog of tadalafil, or a pharmaceutically acceptable salt thereof, with or without another active therapeutic ingredient to address comorbidities, in at least one solvent selected from propylene carbonate, 2-pyrrolidone, dimethyl isosorbide, dimethyl acetamide, n-methyl-2-pyrrolidone (NMP), glacial acetic acid, ethanol, water, oleic acid, and isopropyl myristate.

Sublingual and buccal routes are two different routes of administering therapeutic agents by mouth. As used herein "sublingual" means "under the tongue" and generally refers to a route of administration or formulation given via the mouth or placed under the tongue in such a way that the drug is rapidly absorbed via the blood vessels under the tongue. As used herein, "buccal administration" generally refers to a route of administration that involves placing a drug between the gums and cheek, where it is absorbed into the blood stream. Generally, both sublingual and buccal dosage forms may include tablets, films, or sprays. One form of a sublingual tablet can be a liquisolid formulation wherein a liquid drug solution or suspension is converted into a dry, non-adherent, free-flowing and readily compressible powder by blending with selected powder excipients, carriers, and/or coating materials. Urethral or transurethral administration is a form of transmucosal drug delivery which generally refers to delivery of a drug by passage of the drug through an individual's urethral mucosa and into the bloodstream.

The pharmaceutical formulations of the present disclosure are formulated to disperse the drug, e.g., tadalafil or a derivative or analog of tadalafil, or a pharmaceutically acceptable salt thereof, with or without another active therapeutic agent to treat an associated comorbidity, rapidly when administered by the sublingual or buccal route, without the need for water. They offer a discreet and convenient mode of administration, without risk of choking or difficulty in swallowing that may limit compliance with conventional tablets or capsules in some patients and are of particular relevance in special patient populations such as the elderly with comorbid conditions (e.g., renal impairment or congestive heart failure), and patients with dysphasia. "Conventional tablets or capsules" refers to typical tablet and capsule formulations, which are not formulated for sublingual administration. The present formulations disclosed herein offer convenience, together with superior dosing accuracy and rapid onset of action, which may lead to improved patient compliance due to strong patient preference for buccal, or sublingual dosage forms over conventional solid oral dosage forms, which are not formulated as sublingual dosage forms.

Additionally, the present formulations disclosed herein have enhanced bioavailability of active therapeutic agent or agents, over comparative oral tablet dosage forms. Sublingual and buccal formulations are known to avoid the disadvantages associated with gastrointestinal absorption, such as slow absorption, degradation of the PDE5 inhibitor by gastrointestinal fluids and/or first pass metabolism by the liver.

Another advantage is the reduced effect of food or a meal. Food may decrease the rate and extend of absorption of an oral dosage form and therefore buccal and sublingual dosage forms avoid this potential problem of slowed systemic absorption due to foo ingestion.

Additionally, lower doses are achievable due at least partially to the avoidance of metabolic process associated with gastrointestinal absorption. Sublingual and/or buccal dosage forms would be expected to result in a higher area under the curve (AUC) than similar doses of an agent solely absorbed gastrointestinally. Lower dosages of PDE5 inhibitors may be advantageous in avoiding undesirable side effects such as headache, blindness, and priapism. Moreover, the present sublingual solutions disclosed herein also offer significant cost savings for the patients which contributes to greater utilization and compliance. The solutions have low irritancy for sublingual tissues and are compatible with commercial atomizers.

The pharmaceutical formulations comprise tadalafil or a derivative or analog of tadalafil, or a pharmaceutically acceptable salt thereof, which is a phosphodiesterase type-5 (PDE5) inhibitor. PDE5 enzymes are most prevalent in the penile tissue. PDE5 inhibitors are selective, competitive inhibitors of cGMP which is metabolized through the PDE5 system and acts downstream to decrease intracellular calcium ions ($Ca^{2+}$) in the cavernosal smooth muscles leading to smooth muscle relaxation, reduction of arterial blood drainage, and ultimately attainment and maintenance of an erection. Examples of suitable PDE5 inhibitors include, but are not limited to, tadalafil (Cialis®), sildenafil (Viagra®), vardenafil (Levitra®), avanafil (Stendra®) and udenafil (Zydena®). Sildenafil was the first approved PDE-5 inhibitor for ED and widely used worldwide. Vardenafil, which has a similar molecular structure to sildenafil, has been reported as being more potent than sildenafil and more selective.

In one or more exemplary embodiments of the present disclosure, the PDE5 inhibitor is tadalafil. Tadalafil, (2R, 8R)-2-(1,3-benzodioxol-5-yl)-6-methyl-3,6,17-triazatetracyclo[8.7.0.$0^{3,8}$.$0^{11,16}$]heptadeca-1(10),11,13,15-tetraene-4, 7-dione, has the following chemical structure:

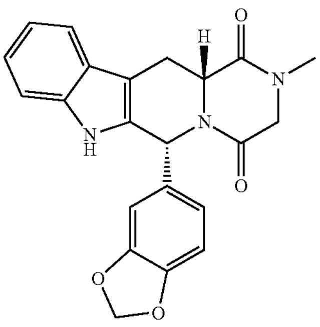

.

Tadalafil differs in molecular structure from sildenafil and vardenafil and has a different pharmacokinetic profile. Compared to sildenafil, tadalafil has greater PDE-5 selectivity and pharmacokinetic properties such as a prolonged half-life, low volume of distribution, slow hepatic clearance, and 80% bioavailability in humans, which supports a prolonged duration of action with once daily administration.

Particularly, in the case of tadalafil, it is insoluble in aqueous media. Unlike other compounds of its class, tadalafil does not form salts, and therefore solubility cannot be increased through salt formation. The present inventor has found that tadalafil can be formulated into a stable solution using a at least one pharmaceutically acceptable liquid vehicle or solvent comprising at least one of propylene carbonate, 2-pyrrolidone, dimethyl isosorbide, dimethyl acetamide, n-methyl-2-pyrrolidone (NMP), glacial acetic acid, ethanol, water, oleic acid, and isopropyl myristate. Thus, the present disclosure encompasses pharmaceutical formulations comprising at least one PDE5 inhibitor, such as tadalafil, with or without other therapeutically active agents for comorbidities associated with ED, in at least one liquid vehicle or solvent selected from propylene carbonate, 2-pyrrolidone, dimethyl isosorbide, dimethyl acetamide, n-methyl-2-pyrrolidone (NMP), glacial acetic acid, ethanol, water, oleic acid, and isopropyl myristate.

Solvents used in the formulations of the present disclosure are aprotic and are solvents in which tadalafil is highly soluble. Propylene carbonate and dimethyl isosorbide may be selected based on having better taste than other solvents. Propylene carbonate or dimethyl isosorbide may be employed in formulations of the present disclosure in the range of from 10-80% by weight. In one or more exemplary embodiments of the present disclosure, propylene carbonate is employed in an amount of 10-60% by weight. In one more exemplary embodiments of the present disclosure, propylene carbonate may be employed in an amount of 20-55% by weight.

N-methyl-2-pyrrolidone (NMP) and 2-pyrrolidone may be selected based on having high tadalafil solubility. N-methyl-2-pyrrolidone (NMP) and 2-pyrrolidone may be employed in formulations of the present disclosure in the range of from 10-60% by weight. In one or more exemplary embodiments of the present disclosure, N-methyl-2-pyrrolidone (NMP) and 2-pyrrolidone may be employed in an amount of 10-50% by weight.

In one or more exemplary embodiments of the present disclosure, ethanol is employed in an amount of 0.1-10% by weight.

In one or more exemplary embodiments, tadalafil is employed in amounts of about 5%, 10%, 15%, or 20% by weight with a solvent of the present disclosure and used for the treatment of ED. In one or more exemplary embodiments, tadalafil is employed in an amount of about 10% by weight in combination with another therapeutic agent, such as oxytocin in an amount of 0.02% by weight, for the treatment of ED. In an exemplary embodiment, the pharmaceutical formulation is an oral mist or spray. Water may be employed in the formulations of the present disclosure in an amount of between 10-15% by weight.

Optionally, the formulation may contain one or more additional pharmaceutical agents, e.g., a dopaminergic drug, a smooth muscle relaxant, a vasoactive drug, or an additive, a pharmaceutically acceptable carrier, or excipient. Suitable additives include, but are not limited to surfactants, stabilizers, antioxidants, flavorings, and sweeteners.

Surfactants may be employed to minimize the risk of precipitation after sublingual administration and to enhance drug permeation across the bio membrane. Suitable surfactants may include, but are not limited to, poloxamer copolymers (e.g., Poloxamer 407®, Poloxamer 188®), polysorbates (Polysorbate 40®, Polysorbate 60® or Polysorbate 80), glyceryl monolaurate, glyceryl monostearate, sorbitan monostearate, sorbitan monolaurate, sorbitan monooleate and other pharmaceutically acceptable surfactants compatible with the vehicle composition. The pharmaceutical formulations of the present disclosure may comprise a surfactant in an amount of about 1-10% by weight. In one or more embodiments, the pharmaceutical compositions of the present disclosure comprise about 5% of a poloxamer copolymer. Polaxomer 407® employed in some examples of the present disclosure is a triblock copolymer comprising a central hydrophobic block of polypropylene glycol flanked by two hydrophilic blocks of polyethylene glycol.

Although, tadalafil is chemically stable in the vehicle composition, physical instability as shown by discoloration may be observed. Suitable stabilizers which prevent or minimize discoloration may include, but are not limited to, acetic acid, lactic acid, propionic acid, butyric acid. Suitable antioxidants may include, but are not limited to, tocopheryl acetate, butylated hydroxy toluene, butylated hydroxy anisole, propyl gallate, ascorbic acid and its esters. Suitable flavorings may include, but are not limited to, eucalyptol, dill oil, anise oil, carraway oil, menthol, passion fruit flavor, licorice extract (e.g., MagnaSweet 100®), glutamic acid and its salts, inosinic acid and salts. Suitable sweeteners may include, but are not limited to, sucralose, saccharin, aspartame, acesulfame potassium, steviosides, rebaudiosides, ethyl maltol.

Water may be added in an amount of up to 15% by weight for compatibility with atomizers. For example, propylene carbonate, NMP and 2-pyrrolidone are incompatible with atomizers with consequent pump failure on storage. The addition of water in an amount of about 10% by weight improved compatibility with the pumps. The addition of water in higher amounts may result in precipitation of tadalafil.

Sublingual liquisolid formulations of the present disclosure such as tablets and capsules can include ingredients to convert the liquid to free-flowing powders such as mesoporous silica (e.g., SYLOID® XDP silica), mesoporous dicalcium phosphate (e,g, Firma® Oil). Sublingual liquisolid tablets of the present disclosure nay also include excipients such as binders, lubricants and other tablet forming agents such as copovidone, sodium stearyl fumarate and microcrystalline cellulose in appropriate amounts to form tablets that are stable, have desired hardness, and have desired friability and dissolution properties for sublingual administration. Sublingual liquisolid capsules of the present disclosure may be made by filing hydroxypropyl methylcellulose capsules with the formulations in the desired amounts using usual capsule making and filling methods.

The pharmaceutical formulations may additionally include one or more agents which is therapeutically active for a comorbidity associated with ED. Such comorbidities include, but are not limited to, premature ejaculation, diabetes, hyperlipidemia, obesity, hyperprolactinemia, benign prostatic hyperplasia, cardiovascular disease, hypertension, chronic obstructive pulmonary disease (COPD), lower urinary tract symptoms (LUTS), testosterone deficiency, and depression. Agents which are therapeutically active for comorbidities associated with ED, include but are not limited to, cardiovascular agents, antihypertensives, antidiabetic agents, antilipidemic agents, anti-obesity agents, and antidepressants.

Other agents that may be employed with the PDE5 inhibitor as an agent that is therapeutically active for the treatment of ED include, but are not limited to, dopamine agonists such as apomorphine, ropinirole, and cabergoline. In one or more exemplary embodiments, the pharmaceutical formulation of the present disclosure comprises tadalafil in combination with cabergoline for the treatment of ED. In one or more exemplary embodiments, the pharmaceutical formulation is an oral mist or spray and comprises 10% by weight of tadalafil and 0.5% by weight of cabergoline. In another exemplary embodiment, the pharmaceutical formulation is an oral mist or spray.

Agents that may be employed with the PDE5 inhibitor as an agent that is therapeutically active for treatment of premature ejaculation associated with ED include, but are not limited to, tramadol, cabergoline, apomorphine, dapoxetine, terazosin, paroxetine, ketamine, dextromethorphan, and oxytocin. In an exemplary embodiment, the pharmaceutical formulation of the present disclosure comprises tadalafil in combination with tramadol for the treatment of ED and premature ejaculation associated with ED. Tramadol has been established as an effective drug for the treatment of premature ejaculation. The combination of tadalafil and tramadol is an affordable, low dose formulation which allows for dose titration in the effective management of erectile dysfunction and premature ejaculation. In one or more exemplary embodiments, the pharmaceutical formulation comprises 5% by weight of tadalafil and 17.5% by weight of tramadol. In one or more exemplary embodiments, the pharmaceutical formulation comprises 10% by weight of tadalafil and 12.5% by weight of tramadol. In one or more exemplary embodiments, the pharmaceutical formulation is an oral mist or spray.

In one or more exemplary embodiments of the pharmaceutical formulation of the disclosure which may be used for the treatment of erectile dysfunction and/or premature ejaculation is the combination of tadalafil and apomorphine. In one or more exemplary embodiments, the pharmaceutical formulation comprises 10% by weight of tadalafil and 1% by weight of apomorphine. In another exemplary embodiment of the pharmaceutical formulation of the disclosure that may be used for the treatment of erectile dysfunction and/or premature ejaculation is the combination of tadalafil and an N-methyl-D-aspartate (NMDA) receptor antagonists, such as ketamine or dextromethorphan. In one or more exemplary embodiments, the pharmaceutical formulation comprises 10% by weight of tadalafil and 12.5% by weight of ketamine. In one or more exemplary embodiments, the pharmaceutical formulation comprises 10% tadalafil and 12.5% by weight of dextromethorphan. In one or more exemplary embodiments, the pharmaceutical formulation is an oral mist or spray.

In one or more exemplary embodiments, the pharmaceutical formulation of the present disclosure comprises tadalafil in combination with alpha blockers, such as terazosin for the treatment of ED and premature ejaculation. In clinical studies terazosin has been shown to improve premature ejaculation. In one or more exemplary embodiments, the pharmaceutical formulation comprises 5% by weight tadalafil and 2% by weight terazosin. In one or more exemplary embodiments, the pharmaceutical formulation is an oral mist or spray.

Agents that may be employed with the PDE5 inhibitor as an agent that is therapeutically active for treatment of diabetes associated with ED include, but are not limited to, metformin sulfonylureas such as glyburide, glipizide and glimepiride; meglitinides such as repaglinide and nateglinide; thiazolidinediones, such as rosiglitazone and pioglitazone; DPP-4 inhibitors, such as sitagliptin, saxagliptin and linagliptin; GLP-1 receptor agonists such as exenatide, liraglutide and semaglutide; and SGLT2 inhibitors, such as canagliflozin, dapagliflozin and empagliflozin.

Agents that may be employed with the PDE5 inhibitor as an agent that is therapeutically active for treatment of cardiovascular disease associated with ED include, but are not limited to, angiotensin-converting enzyme (ACE) inhibitors, such as captopril, enalapril, fosinopril, lisinopril, perindopril, quinapril, ramipril and trandolapril; angiotensin II receptor blockers (ARBs) such as candesartan, losartan, valsartan; angiotensin-receptor neprilysin inhibitors (ARNIs) such as sacubitril/valsartan; If Channel blocker, such as ivabradine; beta-adrenergic blockers, such as bisoprolol, metoprolol succinate, and carvedilol; aldosterone antagonists such as spironolactone and Eplerenone; and diuretics, such as furosemide, bumetanide, torsemide, chlorothiazide, amiloride, hydrochlorothiazide or HCTZ, indapamide, metolazone, and triamterene.

Agents that may be employed with the PDE5 inhibitor as an agent that is therapeutically active for treatment of hyperlipidemia associated with ED include, but are not limited to, statins such as atorvastatin, fluvastatin, lovastatin, pitavastatin, pravastatin, rosuvastatin, and simvastatin; bile acid binding resins such as cholestyramine, colesvelam, and colestipol; cholesterol absorption inhibitor such as ezetimibe; fibrates (fenofibrate and gemfibrozil; niacin; and omega-3 fatty acids such as and loscapent ethyl. In one or more exemplary embodiments, the pharmaceutical formulation comprises 10% by weight of tadalafil and 10% by weight of atorvastatin. In another exemplary embodiment, the pharmaceutical formulation is an oral mist or spray.

Agents that may be employed with the PDE5 inhibitor as an agent that is therapeutically active for treatment of hypertension associated with ED include, but are not limited to, diuretics such as furosemide, bumetanide, torsemide, chlorothiazide, amiloride, hydrochlorothiazide or HCTZ, indapamide, metolazone, and triamterene; beta-blockers such as acebutolol, atenolol, betaxolol, bisoprolol, bisoprolol/hydrochlorothiazide, metoprolol tartrate, metoprolol succinate, nadolol, pindolol, propranolol, solotol, and timolol; angiotensin converting enzyme (ACE) inhibitors such as benazepril, captopril, enalapril, fosinopril, lisinopril, moexipril, perindopril, quinapril, ramipril, and trandolapril; angiotensin II receptor blockers (ARBs), such as candesartan, eprosartan, irbesartan, Losartan, telmisartan, and valsartan; calcium channel blockers such amlodipine, diltiazem, felodipine, isradipine, nicardipine, nifedipine, nisoldipine, and verapamil.

Agents that may be employed with the PDE5 inhibitor as an agent that is therapeutically active for treatment of hyperprolactinemia disorders associated with ED include, but are not limited to dopamine agonists, such as cabergoline and bromocriptine. In one or more exemplary embodiments, the pharmaceutical formulation of the present disclosure comprises tadalafil in combination with cabergoline for the treatment of hyperprolactinemia associated with ED. In one or more exemplary embodiments, the pharmaceutical formulation comprises 10% by weight of tadalafil and 0.5% by weight of cabergoline. In one or more exemplary embodiments, the pharmaceutical formulation is an oral mist or spray.

Agents that may be employed with the PDE5 inhibitor as an agent that is therapeutically active for treatment of benign prostatic hyperplasia associated with ED include, but are not limited to, alpha blockers, such as terazosin, alfuzosin, doxazosin, tamsulosin and silodosin; 5-alpha reductase inhibitors such as finasteride and dutasteride. In one or more exemplary embodiments, the pharmaceutical formulation of the present disclosure comprises tadalafil in combination with terazosin for the treatment of ED and benign prostatic hyperplasia associated with ED. Studies have shown that the combination of tadalafil and alpha blockers such as terazosin, is more effective than either ingredient alone in the treatment of benign prostatic hyperplasia with ED. In one or more exemplary embodiments, the pharmaceutical formulation comprises 5% tadalafil by weight and 2% terazosin by weight. In another exemplary embodiment, the pharmaceutical formulation is an oral mist or spray.

Agents that may be employed with the PDE5 inhibitor as an agent that is therapeutically active for treatment of depression associated with ED include, but are not limited to, selective serotonin reuptake inhibitors (SSRIs) such as paroxetine, citalopram, escitalopram, fluoxetine, sertraline; serotonin and norepinephrine reuptake inhibitors (SNRIs) such as desvenlafaxine, duloxetine, levomilnacipran, and venlafaxine; tricyclic antidepressants (TCAs) such as amitriptyline, amoxapine, clomipramine, desipramine, doxepin, imipramine, nortriptyline, protriptyline, and trimipramine; tetracyclic antidepressant such as maprotiline; dopamine reuptake blocker such as bupropion; 5-HT1A receptor antagonist such as vilazodone; 5-HT@ receptor antagonists such as nefazodone and trazodone; 5-HT3 receptor antagonist such as vortioxetine; monoamine oxidase inhibitors (MAOIs) such as isocarboxazid, phenelzine, selegiline, and tranylcypromine; and noradrenergic antagonist such as mirtazapine. In one or more embodiments, the pharmaceutical formulation comprises 5% tadalafil by weight and 7.5% paroxetine by weight. In another exemplary embodiment, the pharmaceutical formulation is an oral mist or spray.

Agents that may be employed with the PDE5 inhibitor as an agent that is therapeutically active for treatment of chronic obstructive pulmonary disease (COPD) associated with ED include, but are not limited to, short-acting bronchodilators such as albuterol, levalbuterol, ipratropium; corticosteroids such as fluticasone, budesonide, and prednisolone; methylxanthines such as theophylline; long-acting bronchodilators such as aclidinium, arformoterol, formoterol, glycopyrrolate, indacaterol, olodaterol, revefenacin, salmeterol, tiotropium and umeclidinium; phosphodiesterase-4 inhibitor such as roflumilast; mucoactive drugs such as carbocysteine, erdosteine, and N-acetylcysteine.

Agents that may be employed with the PDE5 inhibitor as an agent that is therapeutically active for treatment of lower urinary tract symptoms associated with ED include, but are not limited to, alpha-1 blockers such as terazosin, alfuzosin, doxazosin, silodosin, tamsulosin; 5-alpha reductase inhibitors such as finasteride, dutasteride; anticholinergics such as oxybutynin, fesoterodine, darifenacin, tolterodine, solifenacin, trospium; beta-3 adrenergic agonist such as mirabegron.

The disclosure encompasses administration of any type of formulation or dosage unit suitable for application to the mucosal tissue. The formulation may be a dosage form to be placed under the tongue (sublingual formulations), applied to the buccal mucosa (buccal formulations), applied to the urethral mucosa (transurethral formulations), or sprayed into the mouth or under the tongue (oral mist or spray). In one or more embodiments, the formulations comprise a dosage form for application to the sublingual mucosa and a carrier suitable for sublingual drug delivery of the PDE5 inhibitor.

The amount of PDE5 inhibitor administered and the dosing regimen used, will depend on the particular drug selected, the age and general condition of the subject being treated, the severity of the subject's condition, and the judgment of the prescribing physician. Thus, because of patient-to-patient variability, dosages are a guideline only and the physician may adjust doses of the compounds to achieve the level of effective treatment that the physician considers appropriate for the patient. In considering the degree of treatment desired the physician must balance a variety of factors such as the age of the patient and the presence of other diseases or conditions (e.g., cardiovascular disease).

A typical daily dose of PDE5 inhibitor to be administered for at least partial transmucosal, i.e., buccal, urethral, or sublingual, absorption is generally about 0.5 mg to about 100 mg. In one or more exemplary embodiments, the PDE5 inhibitor is present in an amount of about 0.5 mg to about 40 mg. In one or more exemplary embodiments, the PDE5 inhibitor is present in an amount of about 0.5 mg to about 10 mg. In one or more exemplary embodiments, the PDE5 inhibitor is present in an amount of about 0.5 mg to about 5 mg. Depending on the half-life of the PDE5 inhibitor and the availability via the chosen route of administration, the dosing regimen can be modulated in order to achieve satisfactory therapeutic results. Formulations intended to affect both transmucosal and gastrointestinal absorption may encompass higher doses of the PDE5 inhibitor.

The dosage unit will generally contain from approximately 1% to about 40% by weight of at least one PDE5 inhibitor, preferably the PDE5 inhibitor is present in an amount of about 1% to about 30% by weight of the formulation, and more preferably in an amount of about 5 to 20% by weight. The above dosages are exemplary of the average case, but there can be individual instances in which higher or lower dosage ranges may be merited, and such are within the scope of the disclosure.

It may be desirable to incorporate a permeation enhancer in the formulation in order to increase the rate at which the PDE5 inhibitor permeates through the mucosal tissue to which it is applied, e.g., the buccal mucosa, or sublingual mucosa. These permeation enhancers also are referred to as accelerants, adjuvants, and absorption promoters, and are collectively referred to herein as "permeation enhancers." The permeation enhancer includes those compounds with diverse mechanisms of action including those which have the function of improving the solubility and diffusibility of the drug, and those which improve percutaneous absorption by changing the ability of the stratum corneum to retain moisture, softening the skin, improving the skin's permeability, acting as penetration assistants, or changing the state of the skin such as the boundary layer.

Suitable permeation enhancers include, but are not limited to, dimethylsulfoxide ("DMSO"), dimethyl formamide ("DMF"), N,N-dimethylacetamide ("DMA"), decylmethylsulfoxide ("$C_{10}$ MSO"), polyethylene glycol monolaurate ("PEGML"), glycerol monolaurate, lecithin, 1 substituted azacycloheptan-2-ones, alcohols, or surfactants. Surfactants include, but are not limited to, Tergitol®, Nonoxynol-9®, and TWEEN-80®. 1-Substituted azacycioheptan-2-ones include 1-n-dodecylcyclazacycloheptan-2-one (available under the trademark Azone® from Nelson Research & Development Co., Irvine, Calif.) or SEPA® (available from Macrochem Co., Lexington, Mass.).

Optionally, the formulations may include at least one enzyme inhibitor effective to inhibit drug-degrading enzymes which may be present at the site of administration. Enzyme inhibiting compounds may be determined by the skilled artisan by reference to the pertinent literature and/or using routine experimental methods.

Conventional flavoring agents may be used, such as those described in Remington: The Science and Practice of Pharmacy, $20^{th}$ Ed. (Lippincott, Williams, and Wilkins Publishing), which is incorporated herein by reference. The pharmaceutical compositions of the disclosure generally contain from about 0 to 2% by weight of a flavoring agent. Conventional colorants such as dyes and/or pigments may also be used, such as those described in the Handbook of Pharmaceutical Excipients, by the American Pharmaceutical Association & the Pharmaceutical Society of Great Britain, pp. 81-90 (1986), which is incorporated herein by reference. The pharmaceutical compositions of the disclosure generally contain from about 0 to 2% by weight of colorants.

The pharmaceutical formulations of the present disclosure for sublingual or transurethral administration are concentrated so that the therapeutic dose is contained in the smallest volume (less than 0.2 mL) and is administered without precipitation of the drug in the salivary fluids. The solution is also non-irritating.

The present disclosure overcomes the problems of the prior art administrations by providing a formulation for delivering PDE5 inhibitors quickly and achieving rapid bioavailability. Not to be limited by theory, it is believed that buccal and/or sublingual administration of the PDE5 inhibitor can achieve more advantageous pharmacokinetic parameters than oral dosages solely absorbed through the gastrointestinal tract. Because of the route of administration, the formulations and methods of the disclosure achieve a more rapid onset of action and similar AUCs using lesser dosed amounts of the PDE5 inhibitor than the amounts required in conventional solid oral dosage forms, which are not formulated as sublingual dosage forms.

Moreover, the pharmacokinetic profile of the formulations of the disclosure is believed to be superior to the prior art formulations in that the time to reach effective blood levels is believed to be decreased, while the AUC is believed to be equal or similar to gastrointestinally absorbed drugs administered in much higher doses. The rapid delivery of the active agent is believed to allow for a rapid achievement of therapeutic levels and a faster $T_{max}$.

For example, it is believed that the pharmaceutical formulations are capable of dispersing in the mouth in about 1 to about 10 seconds and the PDE5 inhibitor is absorbed in the bloodstream such that therapeutic levels are attained within about 1 to about 5 minutes. Preferably, the PDE5 inhibitor will reach therapeutic levels within 3 minutes or less. The disclosure encompasses pharmaceutical formulations wherein the PDE5 inhibitor is believed to achieve a $C_{max}$ of about 5 μg/L to about 60 μg/L in about 5 minutes to about 10 minutes and an AUC of about 10 μgh/L to about 200 μgh/L.

The formulations of the present disclosure are believed to have a systemic effect over a period from about 2 minutes to about 24 hours. Preferably, the systemic effect is believed to be from about 2 minutes to about 12 hours. Typically, the time for onset is believed to be about 1 minute to about 20 minutes. Preferably, the onset time is believed to be less than about 10 minutes. More preferably, the onset time is believed to be about 3 minutes.

The formulations of the present disclosure may be used to treat a disease state treatable with a PDE5 inhibitor ("a PDE5-treatable condition"). The biochemical, physiological, and clinical effects of PDE5 inhibitors suggest their utility in a variety of diseases in which modulation of smooth muscle, renal, hemostatic, inflammatory, and/or endocrine function is desirable. Diseases treated by PDE5 inhibitors include, but are not limited to, erectile dysfunction, premature ejaculation, female sexual dysfunction, cardiovascular, cerebral stroke, congestive heart failure, cerebrovascular conditions, ischemic heart disease, pulmonary arterial hypertension, acute respiratory distress syndrome, benign prostatic hypertrophy, atherosclerosis, autoimmune diseases, overactive bladder, bladder outlet obstruction, incontinence, cachexia, cancer, diabetes, endarterectomy, diseases characterized by disorders of gut motility, dysmenorrhoea, elevated intra-ocular pressure, glaucoma, glomerular renal insufficiency, hyperglycemia, hypertension, impaired glucose tolerance, inflammatory diseases, insulin resistance syndrome, intestinal motility, macular degeneration, nephritis, optic neuropathy, osteoporosis, peripheral arterial disease, polycystic ovarian syndrome, renal failure, respiratory tract disorders, thrombocythemia, tubular interstitial diseases, and urologic disorders. Urological disorders include female and male sexual dysfunctions.

Allergic disorders associated with atopy include, but are not limited to, urticaria, eczema, or rhinitis.

Cardiovascular diseases include, but are not limited to, atherosclerosis, restenosis, hypertension, acute coronary syndrome, angina pectoris, arrhythmia, a cardiovascular disease associated with hormone replacement therapy, cerebral infarction, cerebral ischemia, conditions of reduced blood vessel patency (e.g., post-percutaneous transluminal coronary or carotid angioplasty, or post-bypass surgery graft stenosis), deep vein thrombosis, disseminated intravascular coagulation syndrome, heart disease, heart failure, migraine, myocardial infarction, peripheral vascular disease, Raynaud's disease, renal ischemia, renal vascular homeostasis, thrombotic or thromboembolytic stroke, venous thromboembolism, pulmonary arterial hypertension, congestive heart failure, myocardial infarction and angina, and prevention of any such cardiovascular condition or event subsequent to a first cardiovascular event (i.e., "secondary prevention").

Diseases characterized by disorders of gut motility include, but are not limited to, irritable bowel syndrome, diabetic gastroparesis, and dyspepsia.

Female sexual dysfunction (FSD) includes, but is not limited to, clitoral dysfunction, female hypoactive sexual desire disorder, female sexual arousal disorder (FSAD), female sexual pain disorder, and female sexual orgasmic dysfunction (FSOD).

Respiratory tract disorders include, but are not limited to, acute respiratory failure, allergic asthma, allergic rhinitis, bronchitis, chronic asthma, reversible airway obstruction, and allergic disorders associated with atopy (such as urticaria, eczema, or rhinitis).

Other medical conditions for which a PDE5 inhibitor is indicated, and for which treatment with the formulations of the present disclosure may be useful include, but are not limited to, pre-eclampsia, Kawasaki's syndrome, nitrate tolerance, multiple sclerosis, diabetic nephropathy, neuropathy including autonomic and peripheral neuropathy and in particular diabetic neuropathy and symptoms thereof (e.g., gastroparesis, peripheral diabetic neuropathy), Alzheimer's disease, psoriasis, skin necrosis, metastasis, baldness, nutcracker oesophagus, anal fissure, hemorrhoids, insulin resistance syndrome, hypoxic vasoconstriction as well as the stabilization of blood pressure during haemodialysis.

Preferably, the diseases treated using the formulations of the disclosure include erectile dysfunction, pulmonary arterial hypertension, congestive heart failure, benign prostatic hypertrophy, myocardial infarction and angina.

It is understood that other combinations may be undertaken while remaining within the scope of the disclosure. While one or more of the PDE5 inhibitors may be used in an application of monotherapy to treat PDE5-treatable conditions, the formulations of the disclosure may be used also in combination therapy. In one or more exemplary embodiments, the formulations of the disclosure are combined with one or more second pharmaceutical agents that are useful for treating other types of disorders, symptoms, or diseases, and in particular comorbidities. For example, the pharmaceutical formulation may be administered with a second pharmaceutical agent that may cause a PDE5-treatable condition as a side effect. One example of such a second pharmaceutical agent is SRRIs, which are useful for treating depression, but which can have various forms of sexual dysfunction as a side effect. SSRIs include, but are not limited to, paroxetine, fluoxetine, sertraline, fluroxamine, citalopram and escitalopram. In an example of the present disclosure, paroxetine is an SSRI that is employed for combination therapy within the scope of the present disclosure.

Typically, drugs that may cause impotence include, but are not limited to, anti-androgens, anti-anxiety drugs, endoenne, anti-cholinergic drugs, anti-nausea, antihypertensives, chemo-therapeutic agents, psychotropics, histamine receptor antagonists, and anti-hyperlipidemics. Endoenne drugs include estrogens, anti-androgens, lutenizing hormone-releasing hormone (LHRH) analogues, and 5 alpha reductase inhibitors. Anti-hypertensive drugs include diuretics, methyldopa, beta blockers, and Ca antagonists. Psychotropic drugs include major tranquilizers, monoamine oxidase (MAO) inhibitors, selective serotonin reuptake inhibitors, and tricyclo anti-depressants.

The present disclosure also encompasses combination therapy with a second pharmaceutical agent which is being administered to treat a disease or condition which has, as a symptom or complication, a PDE5-treatable condition. Thus, a PDE5 inhibitor may be administered along with a second pharmaceutical agent intended to treat a condition that has erectile dysfunction as a symptom. Diseases that may cause sexual dysfunction include, but are not limited to, craniopharyngioma, diabetes, epilepsy, hypogonadism, hypertension, ischemic heart disease, multiple sclerosis, and/or peripheral vascular disease. Thus, for example, combination therapies comprising co-administration of an anti-epileptic and a PDE5 inhibitor are within the scope of the present disclosure.

Also, within the scope of the present disclosure are methods of treating a patient in need of such treatment by administering a pharmaceutical formulation as herein described. Such patients include those with a PDE5 treatable condition, those with a condition treatable by a second pharmaceutical agent known to cause a PDE5-treatable condition, and those with a condition which has as a known symptom or secondary effect, a PDE5-treatable condition.

Administration of the PDE5 inhibitor and second pharmaceutical agent in combination typically is carried out over a defined time period. For example, the combination may be administered simultaneously or within minutes, hours, days, or weeks depending upon the combination selected.

Combination therapy is intended to embrace administration of the PDE5 inhibitor and second pharmaceutical agent either in a substantially simultaneous manner or a sequential manner. For example, substantially simultaneous administration can be accomplished by administering to a subject a single dosage form, or the two may be separately administered, each in its respective dosage form.

As used herein, the term "erectile dysfunction" is intended to include any and all types of erectile dysfunction, including: vasculogenic, neurogenic, endocrinologic and psychogenic impotence, Peyronie's syndrome, premature ejaculation, and any other condition, disease, or disorder, regardless of cause or origin, which interferes with at least one of the three phases of human sexual response, i.e., desire, excitement, and orgasm. As used herein, the term "impotence" is used here in its broadest sense to indicate a periodic or consistent inability to achieve or sustain an erection of sufficient rigidity for sexual intercourse. See, U.S. Pat. No. 5,242,391; U.S. patent publication No. 2003/0139384.

As used herein, the term "permeation enhancer" refers to an agent that accelerates the delivery of the drug through the mucosa.

As used herein, the terms "phosphodiesterase Type 5", and "PDE5" are used interchangeably.

As used herein, the term "orally" is understood to refer to the oral cavity, i.e., the mouth, or to any of the bodily surfaces contained therein. Thus, an "orally disintegrating" formulation or carrier is one that disintegrates in the mouth, whether lingually, sublingually, or buccally.

As used herein, the term "orally disintegrating carrier" means a carrier capable of dissolving, dispersing, or disintegrating, within the oral cavity, including lingually or sublingually, as well as on the walls of the mouth once placed in the mouth and coming into contact with the mucosal tissue of the tongue, cheek, or mouth.

As used herein, the terms "treating" and "treatment" refer to at least one of reduction in severity and/or frequency of symptoms, elimination of symptoms and/or underlying cause, prevention of the occurrence of symptoms and/or their underlying cause, or improvement or remediation of damage. For example, the present method of "treating" erectile dysfunction, as the term is used herein, thus encompasses both prevention of the disorder in a predisposed individual and treatment of the disorder in a clinically symptomatic individual. As used herein, the term "transmucosal" drug delivery means administration of a drug to the mucosal surface of an individual so that the drug passes through the mucosal tissue and into the individual's blood stream. A preferred form of transmucosal drug delivery herein is "buccal" or "transbuccal" drug delivery, which refer to delivery of a drug by passage of the drug through an individual's buccal mucosa and into the bloodstream. Another preferred form of transmucosal drug delivery herein is "sublingual" or "transublingual" drug delivery, which refer to delivery of a drug by passage of the drug through an individual's sublingual mucosa and into the bloodstream. Another preferred form of transmucosal drug delivery herein is "urethral" or "transurethral" drug delivery, which refer to delivery of a drug by passage of the drug through an individual's urethral mucosa and into the bloodstream.

As used herein, the term "oral mist" means a pharmaceutical formulation formulated as a liquid or particulate matter in air, gas, or vapor in the form of a fine mist for therapeutic purposes. The oral mist may be packaged under pressure and contain therapeutically active ingredients intended for topical application, inhalation, or administered by absorption through the mucosal tissue of the mouth.

As used herein, the term "effective" or "therapeutically effective" amount of a drug or pharmacologically active agent means an amount that is sufficient to provide the desired therapeutic effect, e.g., treatment of erectile dysfunction.

As used herein, the term "$C_{max}$" means the maximum value of PDE5 inhibitor concentration in the patient's blood attained after administration of the pharmaceutical formulation.

EXAMPLES

The invention is further described in the context of the following examples, which are presented by way of illustration, but are not intended to limit the invention.

Tadalafil is insoluble in aqueous media and unlike other compounds of its class does not form salts and therefore solubility cannot be increased through salt formation. Tadalafil is soluble in 2-pyrollidone, but the use of 2-pyrollidone as a solvent is limited by color formation, unpalatable taste, and incompatibility with plastic components of metered-dose delivery systems. The present inventor has found that tadalafil is soluble in propylene carbonate with better taste, but like 2-pyrollidone, a solution in propylene carbonate alone is not compatible with atomizers and results in subsequent pump failure upon storage. Compatibility with the pumps was improved with water in an amount of at least 10% weight in volume. However, larger amounts of water greater than 15% resulted in precipitation of tadalafil with 20% Tadalafil solutions.

Selection of compositions including propylene carbonate, 2-pyrrolidone and water resulted in stable, compatible concentrated solution such that the desired dose could be administered in volumes as little as 50 microliters. The presence of the pyrrolidone requires taste masking and the use of sweeteners. Color formation was minimized by the addition of glacial acetic acid (2-5% by weight), butylated hydroxy toluene (0.1 to 0.1% by weight) propyl gallate (0.5-1% by weight) butylated hydroxy anisole (0.02-0.2% by weight), or combinations of these. Additionally, to minimize the risk of precipitation following sublingual administration, a surfactant such as poloxamer was included in the formulation. In vitro dissolution testing showed that the compositions dissolved rapidly in simulated saliva with more than 80% (T80%) less than 2 minutes. See FIG. 1. The resulting composition had increased bioavailability compared to Tadalafil film coated tablets.

Example 1: Preparation of Tadalafil Sublingual Solutions

In order to prepare a solution of Tadalafil and its combinations, the components are listed in Tables below. The components, without the Purified water, were weighed and mixed until a clear solution is formed. Purified Water was added to make up to the volume and the solution was filled into 5 ml atomizer to deliver 50, 100 or 150 microliters per actuation.

Tadalafil, oxytocin, tramadol hydrochloride (all available from Fagron, Inc.), atorvastatin, paroxetine, cabergoline, apomorphine, ketamine dextromethorphan, and testosterone (all available from Sigma-Aldrich or Spectrum Chemical & Laboratory Products, Inc.) were used as source of active ingredients. Propylene carbonate (from Penta Manufacturing Corp.), n-methyl-2-pyrrolidone (Pharmasolve®) (from Ashland, Inc.), glacial acetic acid, oleic acid and Purified Water USP (from Spectrum Chemical & Laboratory Products, Inc) were used as solvents, Poloxamer 407 (from Spectrum Chemical & Laboratory Products) was used as surfactant/solubilizer, spearmint oil, menthol, eucalyptus oil (from Spectrum Chemical & Laboratory Products) and passion fruit flavor (from Bulk Apothecary) were used as flavor enhancers, tocopherol acetate (from Spectrum Chemical & Laboratory Products) as an antioxidant and sucralose (from Spectrum Chemical & Laboratory Products) was used as a sweetener.

TABLE 1

5% Tadalafil Solution

| Ingredients | Amount (% w/v) |
|---|---|
| Propylene carbonate | 52.00 |
| NMP | 14.00 |
| Glacial acetic acid | 2.00 |
| Poloxamer 407 | 5.00 |
| Tadalafil | 5.00 |
| Menthol | appropriate amount |
| Tocopheryl acetate | appropriate amount |
| Sucralose | appropriate amount |
| Ethanol | appropriate amount |
| Passion fruit flavor | appropriate amount |
| Water q.s. | 100.00 |

TABLE 2

10% Tadalafil Solution

| Ingredients | Amount (% w/v) |
|---|---|
| Propylene carbonate | 40.50 |
| Glacial acetic acid | 2.00 |
| NMP | 23.00 |
| Eucalyptol | 2.00 |
| Poloxamer 407 | 5.00 |
| Tadalafil | 10.00 |
| Menthol | appropriate amount |
| Tocopheryl acetate | appropriate amount |
| Sucralose | appropriate amount |
| Passion fruit flavor | appropriate amount |
| Water q.s (mL) | 100.00 |

TABLE 3

| 20% Tadalafil Solution | |
|---|---|
| Ingredients | Amount (% w/v) |
| Propylene carbonate | 8.50 |
| NMP | 50.00 |
| Glacial acetic acid | 2.00 |
| Poloxamer 407 | 5.00 |
| Tadalafil | 20.00 |
| Eucalyptus oil | appropriate amount |
| Tocopheryl acetate | appropriate amount |
| Sucralose | appropriate amount |
| Passion fruit flavor | appropriate amount |
| Water q.s (mL) | 100.00 |

TABLE 4

| 5% Tadalafil/2% Terazosin | |
|---|---|
| Ingredients | Amount (% w/v) |
| Propylene carbonate | 45.00 |
| Ethanol | 10.00 |
| NMP | 15.00 |
| Glacial Acetic acid | 2.00 |
| Poloxamer 407 | 5.00 |
| Tadalafil | 5.00 |
| Terazosin | 2.00 |
| Menthol | appropriate amount |
| Tocopheryl acetate | appropriate amount |
| Sucralose | appropriate amount |
| Magnasweet MM100 | appropriate amount |
| Passion fruit flavor | appropriate amount |
| Water q.s (mL) | 100.00 |

TABLE 5

| 5% Tadalafil/17.5% Tramadol | |
|---|---|
| Ingredients | Amount (% w/v) |
| Propylene carbonate | 26.50 |
| Ethanol | 5.00 |
| NMP | 20.00 |
| Glacial Acetic acid | 2.00 |
| Poloxamer 407 | 5.00 |
| Tadalafil | 5.00 |
| Tramadol | 17.50 |
| Menthol | appropriate amount |
| Tocopheryl acetate | appropriate amount |
| Sucralose | appropriate amount |
| Passion fruit flavor | appropriate amount |
| Water q.s (mL) | 100.00 |

TABLE 6

| 10% Tadalafil/12.5% Tramadol | |
|---|---|
| Ingredients | Amount (% w/v) |
| Propylene carbonate | 21.50 |
| NMP | 30.00 |
| Glacial acetic acid | 2.00 |
| Poloxamer 407 | 5.00 |
| Tadalafil | 10.00 |
| Tramadol | 12.50 |
| Menthol | appropriate amount |
| Tocopheryl acetate | appropriate amount |
| Sucralose | appropriate amount |
| Passion fruit flavor | appropriate amount |
| Water q.s (mL) | 100.00 |

TABLE 7

| 10% Tadalafil/0.02% Oxytocin | |
|---|---|
| Ingredients | Amount (% w/v) |
| Propylene carbonate | 34.00 |
| NMP | 30.00 |
| Glacial acetic acid | 2.00 |
| Poloxamer 407 | 5.00 |
| Tadalafil | 10.00 |
| Oxytocin | 0.02 |
| Eucalyptol | appropriate amount |
| Tocopheryl acetate | appropriate amount |
| Sucralose | appropriate amount |
| Passion fruit flavor | appropriate amount |
| Water q.s (mL) | 100.00 |

TABLE 8

| 10% Tadalafil/0.5% Cabergoline | |
|---|---|
| Ingredients | Amount (% w/v) |
| Propylene carbonate | 34.00 |
| NMP | 30.00 |
| Glacial acetic acid | 2.00 |
| Poloxamer 407 | 5.00 |
| Tadalafil | 10.00 |
| Cabergoline | 0.50 |
| Menthol | appropriate amount |
| Oleic acid | appropriate amount |
| Tocopheryl acetate | appropriate amount |
| Sucralose | appropriate amount |
| Passion fruit flavor | appropriate amount |
| Water q.s (mL) | 100.00 |

TABLE 9

| 10% Tadalafil/10% Atorvastatin | |
|---|---|
| Ingredients | Amount (% w/w) |
| Propylene carbonate | 30.00 |
| NMP | 35.00 |
| Glacial acetic acid | 2.00 |
| Poloxamer 407 | 5.00 |
| Tadalafil | 10.00 |
| Atorvastatin acid | 10.00 |
| Menthol | appropriate amount |
| Tocopheryl acetate | appropriate amount |
| Sucralose | appropriate amount |
| Passion fruit flavor | appropriate amount |
| Water q.s (mL) | 100.00 |

TABLE 10

| 5% Tadalafil/7.5% Paroxetine HCl | |
|---|---|
| Ingredients | Amount (% w/w) |
| Propylene carbonate | 50.00 |
| NMP | 15.00 |
| Glacial acetic acid | 2.00 |
| Poloxamer 407 | 5.00 |
| Tadalafil | 5.00 |
| Paroxetine | 7.50 |
| Menthol | appropriate amount |
| Tocopheryl acetate | appropriate amount |
| Sucralose | appropriate amount |
| Passion fruit flavor | appropriate amount |
| Water q.s (mL) | 100.00 |

TABLE 11

| 10% Tadalafil/1% Apomorphine | |
|---|---|
| Ingredients | Amount (% w/v) |
| Propylene carbonate | 34.00 |
| NMP | 30.00 |
| Glacial acetic acid | 2.00 |
| Poloxamer 407 | 5.00 |
| Tadalafil | 10.00 |
| Apomorphine | 1.00 |
| Menthol | appropriate amount |
| Oleic acid | appropriate amount |
| Tocopheryl acetate | appropriate amount |
| Sucralose | appropriate amount |
| Passion fruit flavor | appropriate amount |
| Water q.s (mL) | 100.00 |

TABLE 12

| 10% Tadalafil/12.5% Ketamine | |
|---|---|
| Ingredients | Amount (% w/v) |
| Propylene carbonate | 21.50 |
| NMP | 30.00 |
| Glacial acetic acid | 2.00 |
| Poloxamer 407 | 5.00 |
| Tadalafil | 10.00 |
| Ketamine | 12.50 |
| Menthol | appropriate amount |
| Tocopheryl acetate | appropriate amount |
| Sucralose | appropriate amount |
| Passion fruit flavor | appropriate amount |
| Water q.s (mL) | 100.00 |

TABLE 13

| 10% Tadalafil/12.5% Dextromethorphan | |
|---|---|
| Ingredients | Amount (% w/v) |
| Propylene carbonate | 21.50 |
| NMP | 30.00 |
| Glacial acetic acid | 2.00 |
| Poloxamer 407 | 5.00 |
| Tadalafil | 10.00 |
| Dextromethorphan | 12.50 |
| Menthol | appropriate amount |
| Tocopheryl acetate | appropriate amount |
| Sucralose | appropriate amount |
| Passion fruit flavor | appropriate amount |
| Water q.s (mL) | 100.00 |

TABLE 14

| 20% Tadalafil/10% Testosterone | |
|---|---|
| Ingredients | Amount (% w/v) |
| Propylene carbonate | 8.50 |
| NMP | 45.00 |
| Glacial acetic acid | 2.00 |
| Poloxamer 407 | 5.00 |
| Tadalafil | 20.00 |
| Testosterone | 10.00 |
| Tocopheryl acetate | appropriate amount |
| Sucralose | appropriate amount |
| Passion fruit flavor | appropriate amount |
| Water q.s (mL) | 100.00 |

Example 2: Preparation of Sublingual Liquisolid Tablets

Sublingual liquisolid tablet formulations of Tadalafil were prepared using the ingredients listed in Table 15 below. Propylene carbonate, NMP, Poloxamer 407®, tadalafil, testosterone and passion fruit flavor were mixed to obtain a clear solution. Firma® oil (dicalcium phosphate) was added and mixed thoroughly to obtain a homogeneous free-flowing powder. The remaining ingredients were added and mixed in thoroughly. The mixture was compressed into 250 mg tablets using 6 mm tooling to a target hardness of 3.5-4.5 kg with friability of less than 100.

TABLE 15

| Tadalafil 15 mg-Testosterone 15 mg Sublingual Liquisolid Tablets | | |
|---|---|---|
| Ingredients | Amount (% w/v) | Amount/tablet (mg) |
| Propylene carbonate | 2.50 | 6.25 |
| NMP | 16.00 | 40.00 |
| Poloxamer 407 | 1.50 | 3.75 |
| Tadalafil | 6.00 | 15.00 |
| Testosterone | 6.00 | 15.00 |
| Tocopheryl acetate | 0.10 | 0.25 |
| Passion fruit flavor | 4.00 | 10.00 |
| Firma ® Oil (Dicalcium phosphate) | 43.00 | 107.50 |
| Sucralose | 0.50 | 1.25 |
| Copovidone | 4.00 | 10.00 |
| Crospovidone | 5.00 | 12.50 |
| Sodium stearyl fumarate | 1.00 | 2.50 |
| Microcrystalline cellulose | 10.40 | 26.00 |
| Total | 100.00 | 250.00 |

Example 3: Preparation of Sublingual Liquisolid Capsules

Sublingual liquisolid capsule formulations of Tadalafil were prepared using the ingredients listed in Table 16 below, propylene carbonate, NMP, glacial acetic acid, Poloxamer 407®, tadalafil, oxytocin, eucalyptus oil, tocopheryl acetate, sucralose and passion fruit flavor were mixed to obtain a clear solution. Firma® oil (dicalcium phosphate) was added and mixed thoroughly to obtain a homogeneous free-flowing powder. The mixture was filled into size 2 hydroxymethyl methylcellulose (HPMC) capsules to contain 200 mg/capsule.

TABLE 16

| Tadalafil 20 mg-Oxytocin 100 mg Sublingual Liquisolid Capsules | |
|---|---|
| Ingredients | Amount (mg) |
| Propylene carbonate | 8.50 |
| NMP | 50.00 |
| Glacial acetic acid | 2.00 |
| Poloxamer 407 | 5.00 |
| Tadalafil | 20.00 |
| Oxytocin | 0.20 |
| Eucalyptus oil | appropriate amount |
| Tocopheryl acetate | appropriate amount |
| Sucralose | appropriate amount |
| Passion fruit flavor | appropriate amount |
| Firma ® oil (dicalcium phosphate) q.s. | 200.00 |

Example 4: Bioavailability of Sublingual Tadalafil

An open label, balanced, randomized, two-treatment, two-sequence, two-period, single dose, crossover, oral relative bioavailability study was conducted comparing a sublingual solution of tadalafil (Example 1 Tadalafil 5% Solution) in accordance with the present disclosure and tadalafil 10 mg tablet (Cialis® FCT) as the reference product in 24 healthy adult human male subjects under fasting condition.

The solution of tadalafil (T), a single spray (single dose) using 1 mL syringe and MAD atomizer (10 mg/0.2 mL) without water, or the reference product (R) Tadalafil 10 mg tablet was administered with 240 mL±2 mL water at ambient temperature in sitting posture. Strictly, no water was administered during sublingual spray administration. The washout interval between doses was 7 days. The duration of the study was 12 days from the day of admission of the first subject till the last sample collection for the last subject, including the washout period of 7 days.

Figure 2:
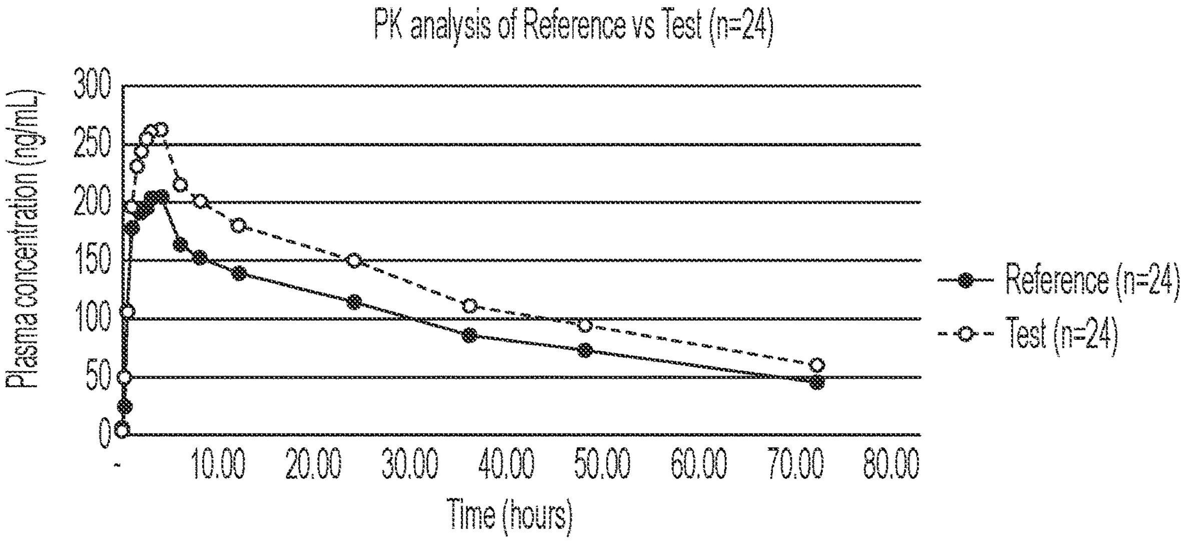
FIG. 2 illustrates comparison of the plasma concentration of the tadalafil sublingual solution formulations of the present disclosure to tadalafil conventional tablets (i.e., not formulated for sublingual administration) compositions.

Blood samples were collected from 0 hr before dosing and up to 72 hours (16 blood samples for each subject) after dosing in each period of the study. Plasma concentrations of tadalafil were analyzed using liquid chromatography—tandem mass spectrometry. FIG. 2 shows the comparison of the plasma concentration of the sublingual tadalafil solution of the present disclosure (Test) compared to the tadalafil tablet formulations (reference). Geometric mean ratios (GMRs) of the sublingual tadalafil solution to tadalafil tablet formulations and their 90% CIs for the pharmacokinetic parameters and statistical analyses were performed for the obtained data to compare the relative oral bioavailability of test formulation to the reference formulation using SAS software Version 9.4, SAS Institute Inc., USA by StatsMetrika Services Private Limited, Bangalore. See Table 17.

TABLE 17

| Parameter | AUC(0-t) (ng*h/mL) | Cmax (ng/mL) | AUC(0-inf) (ng*h/mL) |
|---|---|---|---|
| Least Square Mean (LSM) | | | |
| Test - T | 9.0930 | 5.6599 | 9.4394 |
| Reference - R | 8.8307 | 5.4344 | 9.1507 |
| Geometric LSM* | | | |
| Test - T | 8893.2189 | 287.1146 | 12574.4187 |
| Reference - R | 6841.0670 | 229.1544 | 9420.6488 |
| LSM Difference (T − R) | 0.2623 | 0.2255 | 0.2888 |
| SE Difference | 0.0333 | 0.0454 | 0.0425 |
| p-value (Difference) | <.0001 | <.0001 | <.0001 |
| Geometric LSM Ratio (%) | | | |
| Test - T/Reference - R (%) | 130.00 | 125.29 | 133.48 |
| 90% Confidence Interval (%) Test - T vs. Reference - R | | | |
| Lower Confidence Limit | 122.77 | 115.90 | 124.07 |
| Upper Confidence Limit | 137.65 | 135.45 | 143.59 |
| Intra-Subject Variability (CV %) | 11.57 | 15.83 | 14.82 |
| Inter-Subject Variability (CV %) | 21.74 | 16.44 | 32.97 |
| Power (%) | 99.99 | 99.52 | 99.78 |

Bioequivalence was determined by statistical comparison of $C_{max}$ and $AUC_{0-t}$ for the test and reference products for Tadalafil. The World Health Organization (WHO) considers two formulations to be bioequivalent if the 90% confidence interval for the ratio multisource Test/comparator lie within 80-125% acceptance range for $AUC_{0-t}$ and $C_{max}$. The USDA considers tow products to be bioequivalent if the 90% CI of the relative mean $C_{max}$, $AUC_{(0-t)}$ and $AUC_{(0-\infty)}$ of the test to reference (i.e., sublingual tadalafil formulation to tadalafil tablet formulations) should be within 80% to 125% in the fasting state. The values obtained for relative mean $C_{max}$, $AUC_{(0-t)}$ and $AUC_{(0-\infty)}$ in this study are 136%, 138%, and 137%, respectively.

The pharmacokinetics of the tadalafil sublingual solution formulations of the present disclosure differ significantly from the tadalafil tablet formulations giving higher bioavailability. Additionally, the safety and tolerability profiles of the tadalafil sublingual solution formulation were comparable to those of the tadalafil tablet formulation. Thus, the tadalafil sublingual solution formulations of the present disclosure offer a convenient, discrete treatment option for erectile dysfunction, premature ejaculation, and associate comorbidities.

Further, the disclosure comprises additional notes and examples as detailed below.

Clause 1. A composition, comprising:

an active agent selected from:

(1) tadalafil or a derivative or analog of tadalafil, or a pharmaceutically acceptable salt thereof, or (2) a combination of tadalafil or a derivative or analog of tadalafil, or a pharmaceutically acceptable salt thereof, with a therapeutic agent for the treatment of comorbid diseases or conditions associated with erectile disfunction selected from the group consisting of premature ejaculation, diabetes, cardiovascular disorders, hypertension, hyperlipidemia, obesity, depression, benign prostatic hyperplasia, hyperprolactinemic disorders, chronic obstructive pulmonary disease (COPD), lower urinary tract symptoms (LUTS), and testosterone deficiency; and (b) at least one solvent selected from the group consisting of propylene carbonate, 2-pyrrolidone, dimethyl isosorbide, dimethyl acetamide, N-methyl-2-pyrrolidone, glacial acetic acid, ethanol, water, oleic acid, and isopropyl myristate.

Clause 2. The composition according to clause 1, wherein the solvent comprises propylene carbonate, n-methyl-2-pyrrolidone, and glacial acetic acid.

Clause 3. The composition according to clause 1 or 2, wherein propylene carbonate is employed in an amount of about 10-80% by weight, N-methyl-2-pyrrolidone is employed in an amount of about 10-60% by weight, and glacial acetic acid is employed in an amount of about 1-5% by weight.

Clause 4. The composition according to any one of clauses 1-3, wherein the solvent further comprises ethanol.

Clause 5. The composition according to any one of clauses 1-4, wherein ethanol is in an amount of about 0.1% to 10%.

Clause 6. The composition according to clauses 1-5, further comprising one or more additives selected from the group consisting of surfactants, stabilizers, antioxidants, flavorings, sweeteners, and excipients.

Clause 7. The composition according to claim 6, wherein the one or more additives is a surfactant selected from the group consisting of poloxamer copolymers, polysorbates, glyceryl monolaurate, glyceryl monostearate, sorbitan monostearate, sorbitan monolaurate, and sorbitan monooleate.

Clause 8. The composition according to clause 6 or 7, wherein the surfactant is a poloxamer copolymer.

Clause 9. The composition according to any one of clauses 6-8, wherein the poloxamer copolymer is employed in an amount of about 5% by weight.

Clause 10. The composition according to any one of clauses 6-9, wherein the one or more additives is a stabilizer selected from the group consisting of acetic acid, lactic acid, propionic acid, and butyric acid.

Clause 11. The composition according to any one of clauses 6-10, wherein the one or more additives is an antioxidant selected from the group consisting of tocopheryl acetate, butylated hydroxy toluene, butylated hydroxy anisole, propyl gallate, and ascorbic acid and esters thereof.

Clause 12. The composition according to any one of clauses 6-11, wherein the additives is a flavoring selected from the group consisting of eucalyptol, dill oil, anise oil, carraway oil, menthol, passion fruit flavor, licorice extract, glutamic acid, and salts thereof, and inosinic acid and salts thereof.

Clause 13. The composition according to any one of clauses 6-12, wherein the flavoring is selected from eucalyptol, menthol, passion fruit flavor, and licorice extract.

Clause 14. The composition according to any one of clauses 6-13, wherein the one or more additives is a sweetener selected from the group consisting of sucralose, saccharin, aspartame, acesulfame potassium, steviosides, rebaudiosides, and ethyl maltol.

Clause 15. The composition according to any one of clauses 6-14, wherein the sweetener is sucralose.

Clause 16. The composition according to any one of clauses 6-15, wherein the one or more additives is an excipient selected from the group consisting of free-flowing agents, binders, lubricants, and film-forming agents.

Clause 17. The composition according to any one of clauses 1-16, wherein the composition is a concentrated solution to be administered in a volume less than 0.2 mL.

Clause 18. The composition according to any one of clauses 1-17, wherein the composition is a sublingual, buccal, or transurethral dosage form.

Clause 19. The composition according to any one of clauses 1-17, wherein the composition is a sublingual dosage form which is a liquisolid formulation selected from liquisolid tablets and liquisolid capsules.

Clause 20. The composition according to any one of clauses 1-19, wherein the composition is an oral mist or spray.

Clause 21. The composition according to any one of clauses 1-20, wherein the composition is a transurethral formulation.

Clause 22. The composition according to any one of clauses 1-21, wherein the active agent is tadalafil in amount of from 1 to 30% by weight.

Clause 23. The composition according to any one of clauses 1-21, wherein the active agent is tadalafil is in an amount of from 5% to 20% by weight.

Clause 24. The composition according to any one of clauses 1-21, wherein tadalafil is in an amount of 20% by weight.

Clause 25. The composition according to any one of clauses 1-21, wherein tadalafil is in an amount of 15% by weight.

Clause 26. The composition according to any one of clauses 1-21, wherein tadalafil is in an amount of 10% by weight.

Clause 27. The composition according to any one of clauses 1-21, wherein tadalafil is in an amount of 5% by weight.

Clause 28. The composition according to any one of clauses 1-21, wherein the active agent is a combination of tadalafil and cabergoline.

Clause 29. The composition according to any one of clauses 1-21, wherein the active agent is a combination of tadalafil in amount of 10% by weight and cabergoline in an amount of 0.5% by weight.

Clause 30. The composition according to any one of clauses 1-21, wherein the active agent is a combination of tadalafil and tramadol.

Clause 31. The composition according to any one of clauses 1-21, wherein the active agent is a combination of tadalafil in an amount of 5% by weight and tramadol in an amount of 17.5% by weight.

Clause 32. The composition according to any one of clauses 1-21, wherein the active agent is a combination of tadalafil and apomorphine.

Clause 33. The composition according to any one of clauses 1-21, wherein the active agent is a combination of tadalafil in an amount of 10% by weight and apomorphine in an amount of 1% by weight.

Clause 34. The composition according to any one of clauses 1-21, wherein the active agent is a combination of tadalafil and ketamine.

Clause 35. The composition according to any one of clauses 1-21, wherein the active agent is a combination of tadalafil in an amount of tadalafil in an amount of 10% by weight and ketamine in an amount of 12.5% by weight.

Clause 36. The composition according to any one of clauses 1-21, wherein the active agent is a combination of tadalafil and dextromethorphan.

Clause 37. The composition according to any one of clauses 1-21, wherein the active agent is a combination of tadalafil in an amount of 10% by weight and dextromethorphan in an amount of 12.5% by weight.

Clause 38. The composition according to any one of clauses 1-21, wherein the active agent is a combination of tadalafil and terazosin.

Clause 39. The composition according to any one of clauses 1-21, wherein the active agent is a combination of tadalafil in an amount of 5% by weight and terazosin in an amount of 2% by weight.

Clause 40. The composition according to any one of clauses 1-21, wherein the active agent is a combination of tadalafil and paroxetine.

Clause 41. The composition according to any one of clauses 1-21, wherein the active agent is a combination of tadalafil in an amount of 5% by weight and paroxetine in an amount of 7.5% by weight.

Clause 42. The composition according to any one of clauses 1-21, wherein the active agent is a combination of tadalafil and atorvastatin.

Clause 43. The composition according to any one of clauses 1-21 and 42, wherein the active agent is a combination of tadalafil in an amount of 10% by weight and atorvastatin in an amount of 10% by weight.

Clause 44. The composition according to any one of clauses 1-21, wherein the active agent is a combination of tadalafil and testosterone.

Clause 45. The composition according to any one of clauses 1-21 and 44, wherein the active agent is a combination of tadalafil in an amount of 20% by weight and testosterone in an amount of 10% by weight.

Clause 46. The composition according to any one of clauses 1-21, wherein the active agent is a combination of tadalafil and an antidiabetic agent.

Clause 47. The composition according to any one of clauses 1-21, wherein the active agent is a combination of tadalafil and an anti-hypertensive.

Clause 48. A method for the treatment of erectile dysfunction comprising administering an effective amount of the composition according to any one of clauses 1-45 to a patient in need of such treatment.

Clause 49. A method for the treatment of erectile dysfunction and a comorbid disease or condition associated with erectile dysfunction selected from the group consisting of premature ejaculation, diabetes, cardiovascular disorders, hypertension, hyperlipidemia, obesity, depression, benign prostatic hyperplasia, hyperprolactinemic disorders, chronic obstructive pulmonary disease (COPD), lower urinary tract symptoms (LUTS), and testosterone deficiency, said method comprising administering an effective amount of the composition according to any one of clauses 1-45, to a patient in need of such treatment.

Clause 50. The method according to clause 49, wherein the comorbid disease or condition is premature ejaculation.

Clause 51. The method according to clause 49 or 50, wherein the active agent is a combination of tadalafil and tramadol.

Clause 52. The method according to any one of clauses 49-51, wherein the active agent is a combination of tadalafil in an amount of 5% by weight and tramadol in an amount of 17.5% by weight.

Clause 53. The method according to clause 49, wherein the active agent is a combination of tadalafil and apomorphine.

Clause 54. The method according to clause 49 or 53, wherein the active agent is a combination of tadalafil in an amount of 10% by weight and apomorphine in an amount of 1% by weight.

Clause 55. The method according to clause 49, wherein the active agent is a combination of tadalafil and ketamine.

Clause 56. The method according to clause 49 or 55, wherein the active agent is a combination of tadalafil in an amount of tadalafil in an amount of 10% by weight and ketamine in an amount of 12.5% by weight.

Clause 57. The method according to clause 49, wherein the active agent is a combination of tadalafil and dextromethorphan.

Clause 58. The method according to clause 49 or 57, wherein the active agent is a combination of tadalafil in an amount of 10% by weight and dextromethorphan in an amount of 12.5% by weight.

Clause 59. The method according to clause 49, wherein the comorbid disease or condition is testosterone deficiency.

Clause 60. The method according to clause 49, wherein the active agent is a combination of tadalafil and testosterone.

Clause 61. The method according to clause 49 or 60, wherein the active agent is a combination of tadalafil in an amount of 20% by weight and testosterone in an amount of 10% by weight.

The preceding description is merely illustrative in nature and is in no way intended to limit the disclosure, its application, or uses. As used herein, the phrase at least one of A, B, and C should be construed to mean a logical (A or B or C), using a non-exclusive logical "or." It should be understood that the various steps within a method may be executed in different order without altering the principles of the present disclosure. Disclosure of ranges includes disclosure of all ranges and subdivided ranges within the entire range.

The headings (such as "Background" and "Summary") and sub-headings used herein are intended only for general organization of topics within the present disclosure and are not intended to limit the disclosure of the technology or any aspect thereof. The recitation of multiple examples having stated features is not intended to exclude other embodiments having additional features, or other examples incorporating different combinations of the stated features.

As used herein, the terms "comprise" and "include" and their variants are intended to be non-limiting, such that recitation of items in succession or a list is not to the exclusion of other like items that may also be useful in the devices and methods of this technology.

Similarly, the terms "can" and "may" and their variants are intended to be non-limiting, such that recitation that an embodiment can or may comprise certain elements or features does not exclude other embodiments of the present technology that do not contain those elements or features.

As used herein, the term "about", in the context of concentrations of components of the formulations, typically means+/−5% of the stated value, more typically +/−4% of the stated value, more typically +/−3% of the stated value, more typically, +/−2% of the stated value, even more typically +/−1% of the stated value, and even more typically +/−0.5% of the stated value.

While the foregoing specification illustrates and describes exemplary embodiments, it will be understood by those skilled in the art that various changes may be made, and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure is not limited to the particular embodiment disclosed as the best mode contemplated for carrying out this disclosure, but that the disclosure will include all embodiments falling within the scope of the appended claims.

What is claimed is:

1. A composition, comprising:

(a) an active agent selected from:

(1) tadalafil, or a pharmaceutically acceptable salt thereof, or (2) a combination of tadalafil, or a pharmaceutically acceptable salt thereof, with a therapeutic agent for treatment of comorbid diseases or conditions associated with erectile dysfunction selected from the group consisting of premature ejaculation, diabetes, cardiovascular disorders, hypertension, hyperlipidemia, obesity, depression, benign prostatic hyperplasia, hyperprolactinemic disorders, chronic obstructive pulmonary disease (COPD), lower urinary tract symptoms (LUTS), and testosterone deficiency; and (b) a solvent comprising propylene carbonate, n-methyl-2-pyrrolidone, and glacial acetic acid, wherein the composition is in a sublingual, buccal, or transurethral dosage form, and wherein the sublingual dosage form is a liquisolid formulation.

2. The composition according to claim 1, wherein propylene carbonate is employed in an amount of about 10-60% by weight, and glacial acetic acid is employed in an amount of about 1-5% by weight.

3. The composition according to claim 1, wherein the solvent further comprises ethanol in an amount of about 0.1% to 10%.

4. The composition according to claim 1, further comprising one or more additives selected from the group consisting of surfactants, stabilizers, antioxidants, flavorings, sweeteners, and excipients.

5. The composition according to claim 4, wherein the one or more additive comprise a surfactant, wherein the surfactant is a poloxamer copolymer.

6. The composition according to claim 1, wherein the composition is a concentrated solution to be administered in a volume less than 0.2 ml.

7. The composition according to claim 1, wherein the liquisolid formulation is selected from liquisolid tablets or liquisolid capsules.

8. The composition according to claim 1, wherein the composition is an oral mist or spray.

9. The composition according to claim 1, wherein the active agent is a combination of tadalafil and a therapeutic agent for treatment of premature ejaculation, wherein said agent is selected from the group consisting of tramadol, cabergoline, apomorphine, dapoxetine, terazosin, paroxetine, ketamine, dextromethorphan, and oxytocin.

10. The composition according to claim 1, wherein the active agent is a combination of tadalafil and a therapeutic agent for treatment of hyperlipidemia, wherein said agent is atorvastatin.

11. The composition according to claim 1, wherein the active agent is a combination of tadalafil and a therapeutic agent for treatment of testosterone deficiency, wherein said agent is testosterone.

12. The composition according to claim 1, wherein the active agent is a combination of tadalafil and a therapeutic agent for treatment of diabetes.

13. The composition according to claim 1, wherein the active agent is a combination of tadalafil and a therapeutic agent for treatment of hypertension.

14. A method for treatment of erectile dysfunction comprising administering to a patient in need of such treatment, an effective amount of a composition comprising:

an active agent selected from:

(1) tadalafil, or a pharmaceutically acceptable salt thereof, or (2) a combination of tadalafil, or a pharmaceutically acceptable salt thereof, with a therapeutic agent for treatment of comorbid diseases or conditions associated with erectile dysfunction selected from the group consisting of premature ejaculation, diabetes, cardiovascular disorders, hypertension, hyperlipidemia, obesity, depression, benign prostatic hyperplasia, hyperprolactinemic disorders, chronic obstructive pulmonary disease (COPD), lower urinary tract symptoms (LUTS), and testosterone deficiency; and a solvent comprising propylene carbonate, n-methyl-2-pyrrolidone, and glacial acetic acid, wherein the composition is in a sublingual, buccal, or transurethral dosage form, and wherein the sublingual dosage form is a liquisolid formulation.

15. The method according to claim 14, wherein the composition is a concentrated solution to be administered in a volume less than 0.2 ml.

16. The method according to claim 14, wherein the composition is an oral mist or spray.

* * * * *